| United States Patent [19] | [11] | 4,176,187 |
|---|---|---|
| Ruyle et al. | [45] | Nov. 27, 1979 |

[54] SUBSTITUTED DIHYDROPYRIDINE UREAS

[75] Inventors: William V. Ruyle, Scotch Plains; Michael H. Fisher, Bridgewater, both of N.J.

[73] Assignee: Merck & Co., Inc., Rahway, N.J.

[21] Appl. No.: 920,528

[22] Filed: Jun. 29, 1978

[51] Int. Cl.$^2$ .................... A61K 31/44; C07D 213/75
[52] U.S. Cl. ..................................... 424/263; 546/309
[58] Field of Search ......... 260/295 E, 294.9, 294.8 G, 260/294.8 F, 295.5 D; 424/263; 546/309

[56] References Cited

U.S. PATENT DOCUMENTS

| 3,426,031 | 2/1969 | Fischback | 260/295 E |
| 3,592,900 | 7/1971 | Bicking | 424/263 |
| 3,933,836 | 1/1976 | Yale et al. | 260/294.8 F |
| 3,983,135 | 9/1976 | Rasmussen | 548/312 |
| 3,994,905 | 11/1976 | Kilbourn et al. | 260/294.8 F |
| 4,001,256 | 1/1977 | Callahan et al. | 260/295 E |
| 4,026,938 | 5/1977 | Diana | 260/295 E |
| 4,073,791 | 2/1978 | Fisher et al. | 424/263 |
| 4,120,860 | 10/1978 | Diamond et al. | 260/294.8 F |

OTHER PUBLICATIONS

Smirnoff, Helv. Chim. Acta, 1921, vol. 4, pp. 599–612.
Hunig et al., Ann. 1958, vol. 617, pp. 181–202.
Douglas et al., J. Med. Chem. 1977, vol. 20, pp. 939–943.

Primary Examiner—Alan L. Rotman
Assistant Examiner—Natalia Harkaway
Attorney, Agent, or Firm—Daniel T. Szura; Harry E. Westlake, Jr.

[57] ABSTRACT

Dihydropyridine ureas having antihypertensive activity are disclosed.

26 Claims, No Drawings

SUBSTITUTED DIHYDROPYRIDINE UREAS

BACKGROUND OF THE INVENTION

The present invention is concerned with certain dihydropyridine ureas and their use as antihypertensive agents.

Various chemical agents are available and are effectively used to treat hypertension (high blood pressure). However, the search for new antihypertensive agents continues.

A class of substituted dihydropyridine ureas having antihypertensive activity has been discovered. The mechanism of activity of these ureas appears to be related to their amine e.g. norepinephrine depleting activity.

SUMMARY OF THE INVENTION

Substituted dihydropyridine ureas and their use as antihypertensive agents.

DESCRIPTION OF THE PREFERRED EMBODIMENTS

An embodiment of the present invention is compounds having the formula:

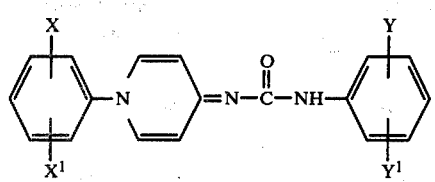

and pharmaceutically acceptable salts thereof wherein
X is H, $C_1$-$C_6$ alkyl, CN, halo Sr or —OR wherein R is $C_1$-$C_6$ alkyl,
$X^1$ is H, $C_1$-$C_6$ alkyl, CN, halo $SR^1$ or $OR^1$ wherein $R^1$ is $C_1$-$C_6$ alkyl,
Y is H, halo, $C_1$-$C_6$ alkyl, CN, $CF_3$, $NO_2$, $COOC_{1-6}$ alkyl, $NR^2R^3$ wherein $R^2$ and $R^3$ are H or $C_1$-$C_6$ alkyl, $SR^4$, $SOR^4$, $SO_2R^4$ or $OR^4$ wherein $R^4$ is $C_1$-$C_6$ alkyl and
$Y^1$ is H, halo, $C_1$-$C_6$ alkyl, CN, $CF_3$, $NO_2$, $COOC_{1-6}$ alkyl, $NR^2R^3$ wherein $R^2$ and $R^3$ are H or $C_1$-$C_6$ alkyl, $SOR^4$, $SO_2R^4$ or $OR^4$ wherein $R^4$ is $C_1$-$C_6$ alkyl
excluding compounds having the formulae:

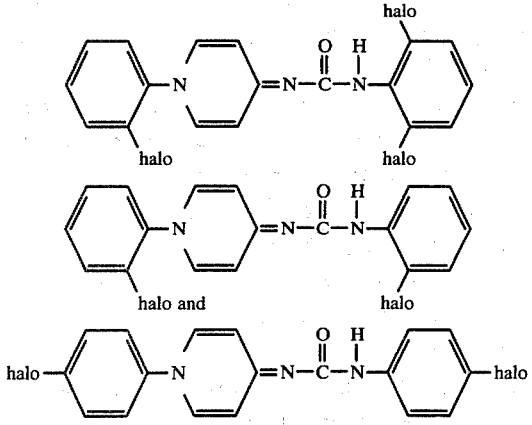

The $C_1$-$C_6$ alkyl substituents, including those represented by R, $R^1$, $R^2$, $R^3$ and $R^4$, are hydrocarbon alkyl groups such as methyl, n-hexyl, t-butyl, isopropyl and the like; the $C_1$-$C_3$ alkyl moieties are preferred.

The halo substituent includes Cl, Br, I and F, with Cl and F being preferred.

Pharmaceutically acceptable salts are principally salts of the formula I compounds with suitable organic or inorganic salts. Useful organic acids are carboxylic acids such as acetic acid, fumaric acid, pamoic acid, succinic acid, maleic acid, citric acid, oxalic acid, pivalic acid, oleic acid, tartaric acid and the like and non-carboxylic acids such as isethionic acid. Useful inorganic acids are exemplified by the hydrohalides e.g. HCl, HI, HBr, sulfuric acid, phosphoric acid, fluorosulfonic acid and the like.

Preferred compounds have the formula

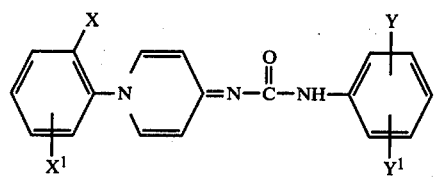

Preferred compounds of formula II have X as halo, $C_1$-$C_6$ alkyl, preferably $C_1$-$C_3$ alkyl, —SR or OR, $X^1$ as H, halo or OR; and Y as halo, $COOR^2$, $SR^3$, $SOR^3$, $SO_2R^3$ or $OR^3$ and $Y^1$ as hydrogen, halo or nitro.

Also included are compounds of formula I or II wherein X is halo or OR and X' is H, halo or OR.

Other preferred compounds have the formula

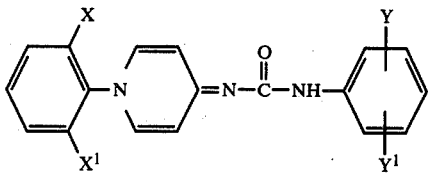

especially where X and $X^1$ are both $C_1$-$C_6$ alkyl, halo or OR. Included among the compounds of formula III are those wherein X and X' are each $C_1$-$C_3$ alkyl, Y is halo and Y' is hydrogen. A more preferred formula III compound has the formula

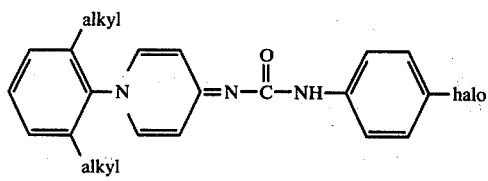

especially where alkyl is $C_1$-$C_3$ preferably $CH_3$, and halo is Cl or F, especially Cl.

More preferred compounds are those having the formula

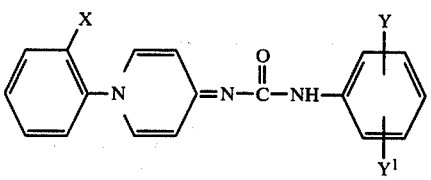

with X preferably being halo or O—$C_1$–$C_3$ alkyl and Y and $Y^1$ both being halo, preferably Cl. In a more preferred embodiment,

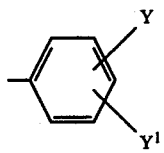

in formula IV has the structure (a)

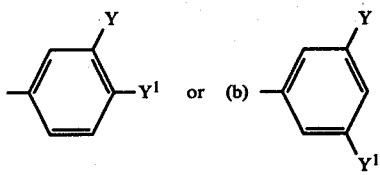

with (a) being more preferred.

The compounds of formula IV also include those wherein X is halo or —$OC_1$–$C_3$ alkyl and those wherein X, Y and Y' are chloro.

More particularly preferred compounds are those having the formula

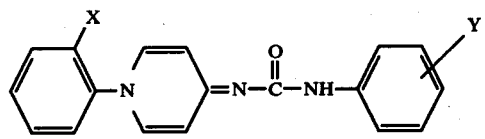

with X preferably being halo or —O—$C_1$–$C_3$ alkyl, and Y preferably being halo, $CF_3$, COO—$C_1$–$C_3$ alkyl, $SR_4$, $SOR^4$, $SO_2R^4$ or $OR^4$, where $R^4$ is $C_1$–$C_3$ alkyl.

Most preferred formula V compounds are represented by

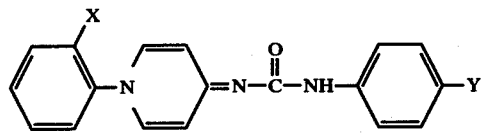

especially where X is Cl, F or —$OC_1$–$C_3$ alkyl and Y is Cl, Br, $COOC_1$–$C_3$ alkyl, —$OC_1$–$C_3$ alkyl, $SC_1$–$C_3$ alkyl or $SO_2C_1$–$C_3$ alkyl.

Following is a table of illustrative examples of the compounds of the present invention:

Table I

Aryl Substituted Dihydropyridine Ureas of the Formula

L—N⟨ ⟩=N—C(=O)—NH—Z

| Ex. | Substituent Group L | Substituent Group Z |
|---|---|---|
| 1 | phenyl | phenyl |
| 2 | 3-cyanophenyl | phenyl |
| 3 | 2-n-hexylphenyl | 3-ethoxyphenyl |
| 4 | 2-methyl-5-ethylphenyl | 4-cyanophenyl |
| 5 | 2-iodophenyl | 3-dimethylaminophenyl |
| 6 | 2,6-dibromophenyl | 3-$CF_3$-phenyl |
| 7 | 3,5-dimethylphenyl | 4-ethylaminophenyl |
| 8 | 2,3-difluorophenyl | 4-$COOC_5H_{11}$-phenyl |
| 9 | 3-ethylphenyl | 3,4-dimethylphenyl |
| 10 | 2-hexyloxyphenyl | 3-propylsulfinylphenyl |
| 11 | 3-propylphenyl | 4-hexylsulfonylphenyl |
| 12 | 2,6-dicyanophenyl | 3,4-dibromophenyl |
| 13 | 2-t-butylphenyl | 4-butylsulfonylphenyl |
| 14 | phenyl | 3-$COOCH_3$-phenyl |
| 15 | 2-isopropylphenyl | 4-aminophenyl |
| 16 | 2,6-diethylphenyl | 3-nitrophenyl |
| 17 | 3-iodophenyl | 4-iodophenyl |
| 18 | 2-cyanophenyl | 4-hexylthiophenyl |
| 19 | 2,5-dichlorophenyl | 3,5-dibromophenyl |
| 20 | 3-ethoxyphenyl | 3,4-dimethylphenyl |
| 20a | 4-ethylthiophenyl | 2-methylphenyl |

The compounds of the present invention have activity as antihypertensive agents. Representative compounds of formula I were tested in spontaneously hypertensive rats and found to have antihypertensive effect(s). This testing indicated that the present compounds would be useful in effectively treating hypertensive humans.

In treating hypertension in humans, the present compounds are administered orally or parenterally in a suitable dosage form. Examples of oral dosage forms are tablets, elixirs, solutions, suspensions, capsules and the like. For parenteral, e.g., intravenous or intraperitoneal, administration, the the suitable dosage forms may be a solution, dispersion, suspension, or emulsion. The pharmaceutical compositions generally are combined with suitable pharmaceutically acceptable compounding ingredients such as binders, sweeteners, excipients, liquid carriers, dispersants and the like. Conventional pharmaceutical compounding techniques and equipment may be used to prepare the compositions.

The effective antihypertensive dosages of the present compounds may range from 0.01 mg. to 500 mg. per patient per day. Dosages of 0.1 mg. to 50 mg. per day are preferred. Daily dosages of 0.25 mg. to 10 mg. are more preferred.

The compounds of the present invention may be prepared by any convenient process.

A useful process is illustrated by the following set of reaction equations:

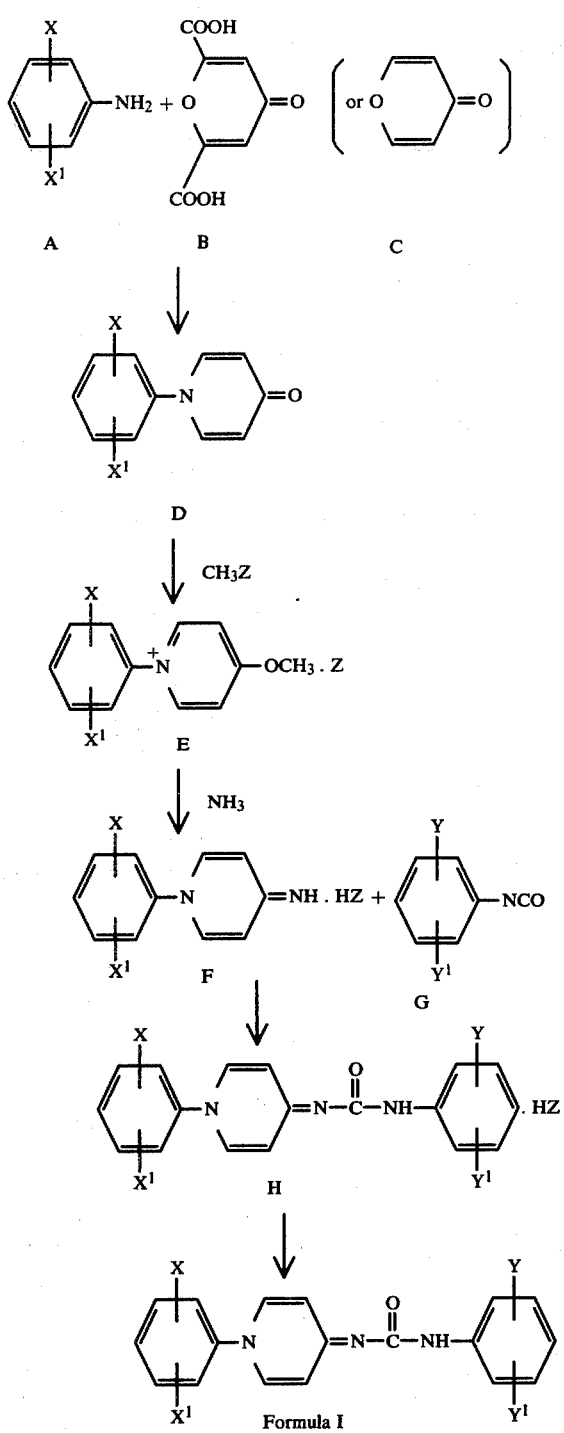

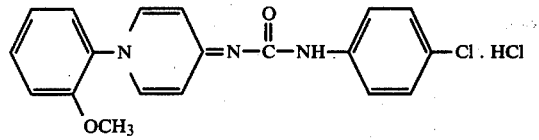

The reaction sequence involves the reaction of an appropriately substituted aniline (A) with either chelidonic acid (B) or γ pyrone (C) to obtain the corresponding substituted 4-(1H)pyridinone (D). [See method described by A. P. Smirnoff in Helv. Chem. Acta 4, 599 (1921)]. This pyridinone (D) is treated with dimethylsulfate or methyl fluorosulfonate in a suitable aprotic solvent (e.g. dimethoxyethane) at elevated temperature e.g. 50°–150° to obtain the corresponding methoxy pyridinium salt (E). This salt (E) is heated with ammonia in a suitable solvent e.g., an alkanol, to produce the corresponding pyridineimine (F). This amine (F) reacts with a suitably substituted phenyl isocyanate (G) to yield the salt (H). This salt may be neutralized to yield the compounds of the present invention (I) as free base. This free base can be converted to a pharmaceutically acceptable salt if desired by treating it with an appropriate organic or inorganic acid using conventional procedures.

The following examples illustrate preparation of representative compounds of the present invention. All temperatures are in °Celsius.

EXAMPLE 21

Preparation of N-(4-Chlorophenyl)-N'-[1-(2-methoxyphenyl)-4(1H)-pyridinylidene] Urea Hydrochloride Step a: 1-(2-methoxyphenyl)-4(1H)-pyridnone A mixture of 30 g (0.148 moles) of chelidonic acid monohydrate and 104 g (0.84 moles) of o-anisidine was heated in an oil bath at 160° for ten minutes, after which evolution of carbon dioxide had stopped. The cooled mixture was added to 600 ml of water and sufficient concentrated HCl was added to bring the pH to approximately 2. The dark mixture was filterd through supercell. The filtrate was made alkaline (pH=12) with sodium hydroxide and was then steam distilled until removal of excess o-anisidine (via the distillate) appeared to be complete. The residual solution was concentrated in vacuo until inorganic salts started to separate, and then it was extracted with 3×500 ml of CHCl₃. After drying with anhydrous Mg SO₄, the CHCl₃ solution was concentrated to about 250 ml and an equal volume of hexane was added. The mixture was chilled and the solid which formed was filtered off. This solid was recrystallized from CHCl₃-hexane yielding 19.8 g of product material. To remove a small amount of o-anisidine which contaminated this material, it was subjected to steam distillation. The hot, residual aqueous solution was then filtered and cooled. A total of 15 g (50% yield) of the hemi-hydrate of 1-(2-methoxyphenyl)-4(1H)-pyridinone was obtained. The compound was obtained in anhydrous form by azeotropic distillation with benzene. The melting point of the anhydrous 1-(2-methoxyphenyl)-4(1H)-pyridinone was 95°–97°.

Step b: 1-(2-methoxyphenyl)-4-methoxy-pyridinium methosulfate:

A solution of 4.02 g (20 millimoles) of 1-(2-methoxyphenyl)-4(1H)-pyridinone in 20 ml. of 1,2-dimethoxyethane (DME) was heated to reflux and a solution of 2.5 g (20 millimoles) of dimethylsulfate in 10 ml of DME was added over a 10 minute period. After refluxing for 30 minutes more, the mixture was cooled and the resulting solid was filtered off; 6.2 g (95% yield) of 1-(2-methoxyphenyl)-4-methoxy-pyridinium methosulfate (M.P.=120°–131°) were obtained.

Using the method of step (b), the following 4-methoxy pyridinium compounds were prepared:
1-(2'-fluorophenyl)-4-methoxypyridinium methosulfate
1-(2'-chlorophenyl)-4-methoxypyridinium methosulfate 1-(2',6'-dimethylphenyl)-4-methoxypyridinium methosulfate
1-(4'-chlorophenyl)-4-methoxypyridinium methosulfate The corresponding fluorosulfonate salts are prepared by using methyl fluorosulfonate in place of dimethyl sulfate in the step (b) reaction.

Step c: 1-(2-methoxyphenyl)-4(1H)-pyridineimine methosulfate

Ammonia gas was passed into an ice-cooled solution of 3.27 g (10 millimoles) of 1-(2-methoxyphenyl)-4-methoxypyridinium methosulfate in 15 ml of methanol units 2 g of ammonia had been adsorbed. After standing at 25° for 72 hours, the reaction mixture was concentrated, the residue was triturated with cold ethanol and the product was filtered off: 3.01 g (96% yield) of 1-(2-methoxyphenyl)-4(1H)-pyridineimine methosulfate (M.P.=121°-124°) were obtained.

Other pyrimidineimines prepared from corresponding 4-methoxypyridinium compounds using the step C procedure were 1-(2'-fluorophenyl)-4(1H)-pyrimidineimine methosulfate
1-(2'-chlorophenyl)-4(1H)-pyrimidineimine methosulfate
1-(2',6'-dimethylphenyl)-4(1H)-pyrimidineimine methosulfate
1-(4'-chlorophenyl)-4(1H)-pyrimidineimine methosulfate

Step d: N-(4-chlorophenyl)-N'-[1-(2-methoxyphenyl)-4(1H)-pyridyliden]urea hydrochloride A solution of 2.64 g (8.5 millimoles) of 1-(2-methoxyphenyl)-4(1H)-pyridineimine methosulfate and 1.53 g (10 millimoles) of p-chlorophenylisocyanate in 5 ml of dimethylformamide was heated on a steam bath (about 95°) for 2 hours. The reaction mixture was then concentrated in vacuo to an oil. This oil was crude N-(4-chlorophenyl)-N'-[1-(2-methoxyphenyl)-4(1H)-pyridylidene]urea methosulfate. This compound could be crystallized only with difficulty. Therefore, this oil was neautralized by partitioning between methylene chloride and 1 N NaOH. The organic layer was dried and evaporated, and the residue (free base) was taken up in 15 ml of ethanol. To the cold, stirred ethanolic solution was added 1.5 ml of concentrated HCl. After chilling for 30 minutes, 2.65 g (80% yield) of N-(4-chlorophenyl)-N'-[1-(2-methoxyphenyl)-4(1H)-pyridylidine]urea hydrochloride [M.P.=228°-230° (dec.)] were obtained. This product was recrystallized from ethanol/water (6/1) raising the M.P. to 230°-232° (dec).

Using substantially the same 4 step process as in Example 21 but substituting an appropriate substituted aniline for the o-anisidine in step a and the appropriate substituted phenylisocyanate in step (d), the following substituted ureas of the present invention were prepared:

| EXAMPLE | COMPOUND | M.P.(°C.) |
|---|---|---|
| 22 | N-(4-chlorophenyl)-N'-[1-[2-fluorophenyl)-4(1H)-pyridinylidene]urea | 187°-188° (dec.) |
| 23 | N-(4-chlorophenyl)-N'-[1-(2-fluorophenyl)-4(1H)-pyridinylidene]urea fluorosulfonate | — |
| 24 | 1-(2-chlorophenyl)-4-(4-chlorophenylaminocarbonylamino)-1,4-dihydropyridine | 155°-157° (dec.) |
| 25 | N-(4-chlorophenyl)-N-[1-(2-chlorophenyl)-4(1H)-pyridinylidene]urea fluorosulfonate | — |
| 26 | N-(4-chlorophenyl)-N-[1-(2,6-dimethylphenyl)-4(1H)-pyridinylidene]urea | 131°-133° (dec.) |
| 27 | N-[1-(2-chlorophenyl)-4(1H)-pyridinylidene)]-N'-(4-(methylthio)phenyl]urea | 160°-162° (dec.) |
| 28 | N-[1-(2-chlorophenyl)-4(1H)-pyridinylidene]-N'-(4-methylthio)phenyl]urea fluorosulfonate | — |
| 29 | N-[1-(2-chlorophenyl)-4(1H)-pyridinylidene]-N'-(3,4-dichlorophenyl]urea | 147°-149° C. |
| 30 | N-[1-(2-chlorophenyl)-4(1H)-pyridinylene]-N'-(3,4-dichlorophenyl]urea fluorosulfonate | — |
| 31 | N-1-(2-chlorophenyl)-4(1H)-pyridinylidene)-N'-(4-methoxyphenyl)urea | 183°-184° (dec.) |
| 32 | Ethyl 4-[1-(2-chlorophenyl)-4(1H)-pyridinylidene amino carbonyl amino benzoate | 178°-180° (dec.) |
| 33 | N-[1-(2-chlorophenyl)-4(1H)-pyridinylidene]-N'-(4-nitrophenyl)urea | — |
| 34 | N-[1-(2-chlorophenyl)-4(1H)-pyridinylidene]N'-(3-trifluoromethyl)phenyl]urea | — |
| 35 | N-(3-chlorophenyl)-N-[1-(2-chlorophenyl)-4(1H)-pyridinylidene]urea | 134°-135° (dec.) |
| 36 | N-[1-(2-chlorophenyl)-4(1H)-pyridinylidene]-N'-[4-(methylsulfonyl)phenyl]urea | 188°-190° (dec.) |
| 37 | N-[1-(2-chlorophenyl)-4(1H)-pyridinylidene]-N'-[4-(methylsulfonyl)phenyl]urea | 197°-199° (dec.) |
| 38 | N-(4-bromophenyl)-N'-[1-(2-chlorophenyl)-4(1H)-pyridinylidene]urea | 168°-169° (dec.) |
| 39 | N-[1-(2-methoxyphenyl)-4(1H)-pyridinylidene] -N'-[4-methylsulfinyl)phenyl]urea | — |
| 40 | N-[1-(2-methoxyphenyl)-4(1H)-pyridinylidene]-N'-8 4-(methylthio)phenyl]urea | 163°-165° |

While Examples 21–40 utilized chelidonic acid as a reactant in step a, similar results are obtained if γ-pyrone is used in place of the chelidonic acid.

As pointed out above, representative examples were tested and found to have antihypertensive activity in an animal model (spontaneously hypertensive rat) using a recognized test protocol.

Claims to the invention follow.

What is claimed is:

1. A compound having the formula

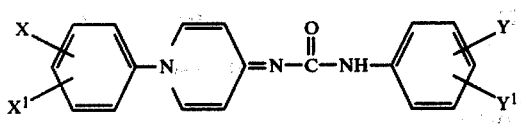

and pharmaceutically acceptable salts thereof wherein

X is H, $C_1$-$C_6$ alkyl, CN, halo, SR or —OR wherein R is $C_1$-$C_6$ alkyl, $X^1$ is H, $C_1$-$C_6$ alkyl, CN, halo, $SR^1$ or $OR^1$ wherein $R^1$ is $C_1$-$C_6$ alkyl, Y is H, halo, $C_1$-$C_6$ alkyl, CN, $CF_3$, $NO_2$, $COOC_1$-$C_6$ alkyl, $NR^2R^3$ wherein $R^2$ and $R^3$ are H or $C_1$-$C_6$ alkyl, $SR^4$, $SOR^4$, $SO_2R^4$ or $OR^4$ wherein $R^4$ is $C_1$-$C_6$ alkyl and $Y^1$ is H, halo, $C_1$-$C_6$ alkyl, CN, $CF_3$, $NO_2$, $COOC_1$-$C_6$ alkyl, $NR^2R^3$ wherein $R^2$ and $R^3$ are H or $C_1$-$C_6$ alkyl, $SOR^4$, $SO_2R^4$ or $OR^4$ wherein $R^4$ is $C_1$-$C_6$ excluding compounds having the formulae:

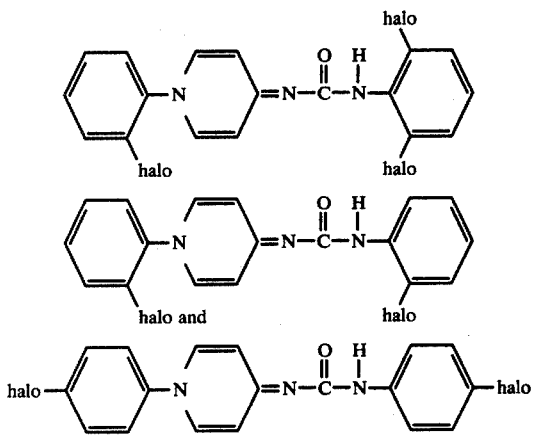

2. A compound of claim 1 wherein X is halo or OR and $X^1$ is H, halo or OR.

3. A compound of claim 2 wherein R is $C_1$-$C_3$ alkyl.

4. A compound of claim 1 having the formula

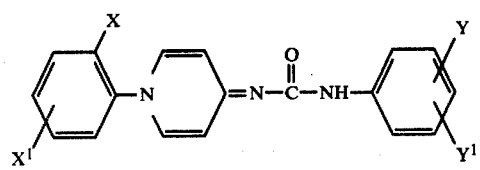

5. A compound of claim 4 wherein X is halo or OR and $X^1$ is H, halo or OR.

6. A compound of claim 5 wherein Y is halo, $COOR^2$, $SR^3$, $SOR^3$, $SO_2R^3$ or $OR^3$ and $Y^1$ is H, halo or nitro.

7. A compound of claim 1 having the formula

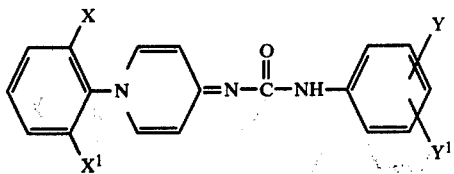

8. A compound of claim 7 wherein X and $X^1$ are each halo, $C_1$-$C_6$ alkyl or OR.

9. A compound of claim 8 wherein X and $X^1$ are each $C_1$-$C_3$ alkyl, Y is halo and $Y^1$ is H.

10. A compound of claim 1 having the formula

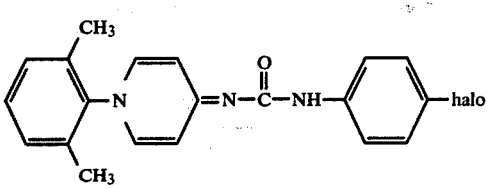

11. A compound of claim 10 wherein said halo is Cl.

12. A compound of claim 1 having the formula

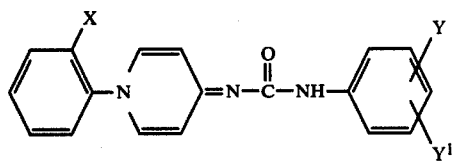

13. A compound of claim 12 wherein

has the configuration

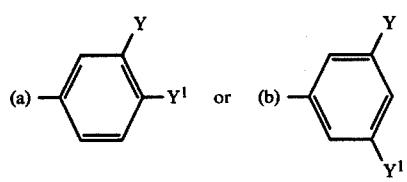

14. A compound of claim 13 wherein X is halo or O—$C_1$-$C_3$ alkyl.

15. A compound of claim 14 wherein Y and $Y^1$ are both halo.

16. A compound of claim 14 wherein

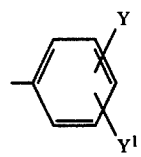

has configuration (a) and X, Y and $Y^1$ are chloro.

17. A compound of claim 12 having the formula

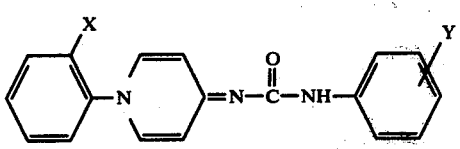

18. A compound of claim 17 wherein X is halo or O—$C_1$-$C_3$ alkyl and Y is halo, $CF_3$, $COOC_1$-$C_3$ alkyl, $SR^4$, $SOR^4$ $SO_2R^4$ or $OR^4$ wherein $R^4$ is $C_1$-$C_3$ alkyl.

19. A compound of claim 18 wherein

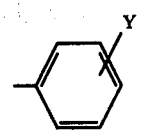

has the configuration

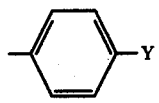

20. A compound of claim 19 wherein X is Cl, F or O—$C_1$-$C_3$ alkyl and Y is Cl, Br, $COOC_1$-$C_3$ alkyl, O—$C_1$-$C_3$ alkyl, —$SC_1$-$C_3$ alkyl or $SO_2$ $C_1$-$C_3$ alkyl.

21. A compound of claim 20 wherein X is $OCH_3$ and Y is Cl.

22. A compound of claim 20 wherein X is F and Y is Cl.

23. The hydrochloride salt of the claim 21 or 22 compound.

24. A method of treating hypertension which comprises administering orally or parenterally to a human in need of such treatment an antihypertensive effective amount of a compound of claim 1.

25. A pharmaceutical composition for treating hypertension containing an effective amount of compound of claim 1 and suitable, pharmaceutically acceptable compounding ingredient.

26. The fluorosulfonate salt of the claim 21 or 22 compound.

* * * * *